United States Patent

Brown et al.

[11] 3,961,057
[45] June 1, 1976

[54] BENZOPYRANO(3,4-C)PYRIDINE BRONCHODILATORS

[75] Inventors: Richard E. Brown, Hanover; John Shavel, Jr., Mendham, both of N.J.

[73] Assignee: Warner-Lambert Company, Morris Plains, N.J.

[22] Filed: Jan. 3, 1975

[21] Appl. No.: 538,424

Related U.S. Application Data

[60] Division of Ser. No. 343,613, March 23, 1973, abandoned, which is a continuation-in-part of Ser. No. 122,498, March 9, 1971, abandoned.

[52] U.S. Cl.............................. 424/248; 424/246; 424/250; 424/263
[51] Int. Cl.²...................................... A61K 31/535
[58] Field of Search ............ 424/246, 248, 250, 263

[56] References Cited
UNITED STATES PATENTS

| | | | |
|---|---|---|---|
| 3,396,165 | 8/1968 | Bolger | 260/295.5 T |
| 3,429,889 | 2/1969 | Shulgin et al. | 260/295 T |
| 3,514,464 | 5/1970 | Pars et al. | 424/266 |
| 3,689,497 | 9/1972 | Brown et al. | 260/295 T |

*Primary Examiner*—Norman A. Drezin
*Attorney, Agent, or Firm*—Albert H. Graddis; Frank S. Chow; George M. Yahwak

[57] ABSTRACT

Substituted benzopyrano[3,4-c]pyridines having the following structural formula are disclosed:

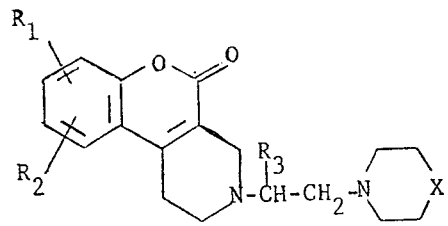

I

In the above formula, $R_1$ and $R_2$ are hydrogen, a hydroxyl group or a lower alkoxyl group of from 1 to 6 carbon atoms; $R_3$ is hydrogen or a lower alkyl group of from 1 to 6 carbon atoms and X is an oxygen atom, a sulfur atom, a methylene group or a nitrogen atom substituted by hydrogen, a lower alkyl group of from 1 to 6 carbon atoms or a lower alkanoyl group of from 1 to 6 carbon atoms. The compounds of this invention are prepared by reacting an $R_1$, $R_2$-substituted phenol with a 3-carbethoxy-4-piperidone in the presence of an acid catalyst to give an intermediate $R_1$, $R_2$-substituted benzopyrano[3,4-c]pyridine. N-aminoalkylbenzopyrano[3,4-c]pyridines are obtained by treating the benzopyrano[3,4-c]pyridine with an appropriately substituted alkyl halide. The compounds of this invention are useful as bronchodilators for the treatment of bronchial asthma.

10 Claims, No Drawings

BENZOPYRANO(3,4-C)PYRIDINE BRONCHODILATORS

This is a division, of application Ser. No. 343,613 filed Mar. 23, 1973 now abandoned which in turn is a continuation-in-part of application Ser. No. 122,498 filed Mar. 9, 1971 now abandoned.

The present invention relates to a new class of benzopyrano[3,4-c]pyridines having the following structural formula:

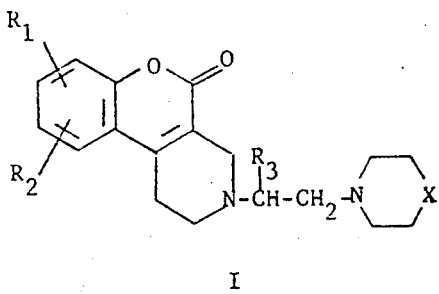

I wherein $R_1$ and $R_2$ are hydrogen, a hydroxyl group or a lower alkoxyl group of from 1 to 6 carbon atoms; $R_3$ is hydrogen or a lower alkyl group of from 1 to 6 carbon atoms and X is an oxygen atom, a sulfur atom, a methylene group or a nitrogen atom substituted by hydrogen, a lower alkyl group of from 1 to 6 carbon atoms or a lower alkanoyl group of from 1 to 6 carbon atoms.

The compounds of this invention are active as bronchodilators and as such protect the guinea pig against histamine, serotonin or acetylcholine induced bronchospasm for a duration of up to 4 hours at an oral dose of 10 mg/kg. Thus, the aforementioned compounds are more effective than aminophylline, a valuable drug for the treatment of bronchial asthma and pulmonary edema, which protects the guinea pig against histamine, serotonin or acetyl choline induced bronchospasm for less than 2 hours at a dose of 100 mg/kg. In addition, the compounds disclosed in this invention reverse pilocarpine or histamine bronchoconstriction in the dog for a duration of up to 1 hour at an oral dose of 10 mg/kg. The bronchodilator activity exhibited by the N-substituted benzopyrano[3,4-c]pyridines described in this invention is the result of a direct smooth muscle relaxant effect on the bronchial tree as shown by in vitro experiments on guinea pig trachea. In these experiments, the N-substituted benzopyrano[3,4-c]pyridines are approximately 75 times more active than aminophylline in relaxing tracheal smooth muscle.

The compounds of this invention are useful for the treatment of bronchial asthma. Generally speaking, a dose of about 500 mg to 1000 mg several times daily is recommended for mammals weighing about 70 kilograms. The compounds can be administered orally or by parenteral administration.

In order to use these compounds they are formulated with pharmaceutically acceptable excipients such as lactose, starch, powdered sugar and the dosage forms can be tablets, capsules and the like. The dosage regimen can be varied according to the condition being treated by methods well known to the healing arts.

According to the present invention, the compounds of this invention are prepared in accordance with the following reaction scheme:

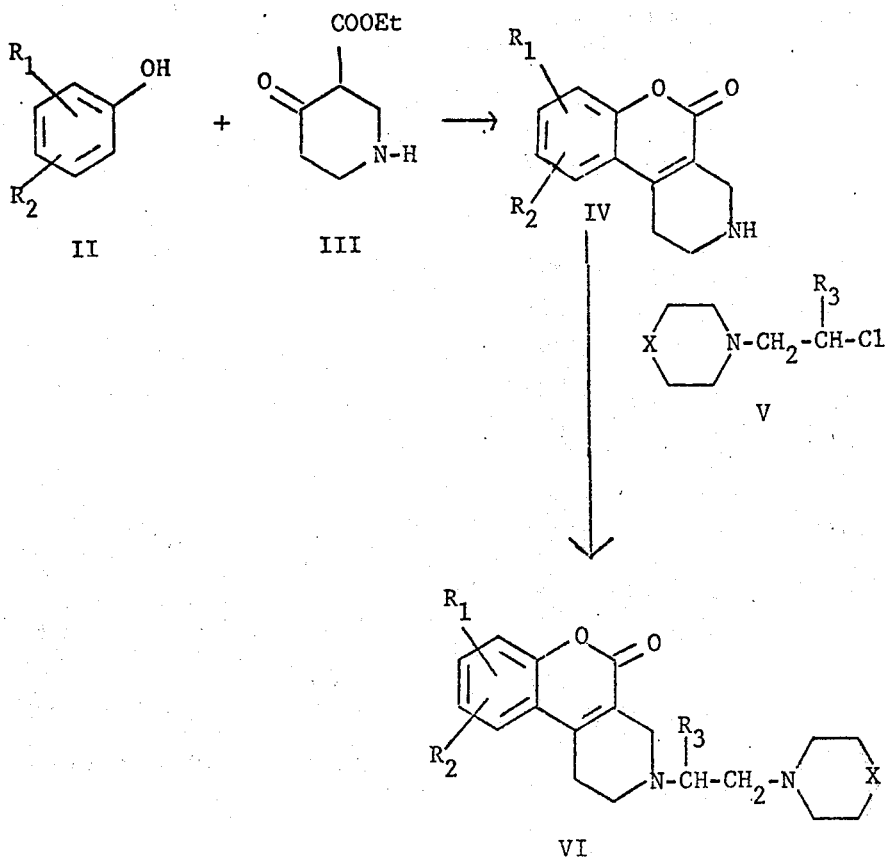

In the first step, an $R_1$, $R_2$-substituted phenol is treated with 3-carbethoxy-4-piperidone in the presence of an acid catalyst to give a benzopyrano[3,4-c]pyridine intermediate corresponding to structure IV above. The starting phenolic compound II, such as, for example, m-methoxyphenol, 3,4-dimethoxyphenol, 2,3-dimethoxylphenol, 3,5-dimethoxyphenol, and so on, are known compounds and are available commercially such as from Aldrich Chemical Company.

Exemplary of the acid catalysts which can be employed in this reaction are sulfuric acid, phosphoric acid, phosphorous oxychloride, phosphorous pentoxide, polyphosphoric acid, boron fluoride and the like.

Conversion of intermediates of structure IV to the final products corresponding to structure VI is accomplished by treatment with the appropriate 2-aminoalkyl halide of structure V wherein $R_3$ is hydrogen or a lower alkyl group of from 1 to 6 carbon atoms and X is an oxygen atom, a sulfur atom, a methylene group or a nitrogen atom substituted by hydrogen, a lower alkyl group of from 1 to 6 carbon atoms or a lower alkanoyl group of from 1 to 6 carbon atoms.

To prepare the N-aminoalkylbenzopyrano[3,4-c]pyridines of structure VI wherein $R_1$ and $R_2$ are ethoxy and $R_3$ and X are as defined in the preceding paragraph, the corresponding dimethoxy analogs, compounds of structure VI wherein $R_1$ and $R_2$ are methoxy and $R_3$ and X are as before, are demethylated with 48% hydrobromic acid to the dihydroxy derivatives of structure VI wherein $R_1$ and $R_2$ are hydroxyl groups followed by ethylation with diethylsulfate in the presence of a base such as potassium carbonate.

Although in the following examples only a representative number of compounds are illustrated, it is obvious to those skilled in the art that by employing appropriate starting materials, other compounds which fall within the scope of this invention can be prepared following the procedures described herein.

The following examples are included to further illustrate the practice of this invention. All degrees are given in the Centigrade scale.

EXAMPLE 1

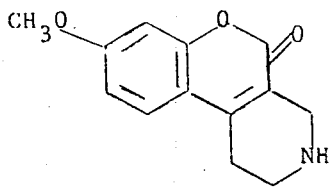

1,2,3,4-Tetrahydro-8-methoxy-5H-[1]benzopyrano-[3,4-c]pyridin-5-one. A mixture of 31.0 g of m-methoxyphenol (0.25 m) and 41.5 g of 3-carbethoxy-4-piperidone hydrochloride (0.2 m) was cooled in an ice bath and treated with 50 ml of con. $H_2SO_4$ in 20 min. with stirring and protection from moisture. After stirring for 20 hours at room temperature, the reaction was cooled and treated with ice water to 250 ml volume. Concentrated $NH_4OH$ was added to pH 9 and the resulting precipitate was filtered, washed with water, and dried in vacuo affording 41.0 g (88%) of crude product. Crystallization from ethanol afforded analytical, constant melting material, mp 171°–80°C.

Anal. Calcd for $C_{13}H_{13}NO_3$: C, 67.52; H, 5.67; N, 6.06. Found: C, 67.71; H, 5.72; N, 6.19

HCl (¼ $C_2H_5OH$), mp 248°–50°C.

Anal. Calcd for $C_{13}H_{13}NO_3HCl$ ¼ $C_2H_5OH$: C, 57.86; H, 5.93; H, 5.00; Cl, 12.65. Found: C, 57.51; H, 5.66; N, 5.11; Cl, 12.65.

EXAMPLE 2

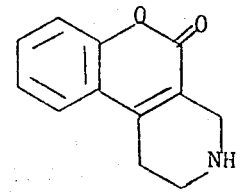

1,2,3,4-Tetrahydro-5H-[1]benzopyrano[3,4-c]pyridin-5-one. A mixture of 18.8 g (0.2 m) of phenol and 20.7 g (0.1 m) of 3-carbethoxy-4-piperidone HCl was cooled in an ice bath and treated with 75 cc of 73% v/v $H_2SO_4$ in one-half hr. with stirring and protection from moisture. After stirring 4 days at room temperature the reaction was chilled and treated with an additional 10 g (0.106 m) of phenol. After 5 days a second 10 g portion of phenol was added. After stirring 6 days the reaction was treated with 100 g of ice and conc. $NH_4OH$ to pH 8–9. The resultant gum was stirred with 100 cc $CHCl_3$ for one-half hr. and was filtered. The filtrate was evaporated and the resultant gum was triturated with pet ether followed by ethyl ether. The resultant solid was crystallized from 100 cc 3N HCl affording 2.3 g (10%) of product mp. 330°–5°C.

Anal. Calcd for $C_{12}H_{11}NO_2HCl$: C, 60.64; H, 5.09; N, 5.89; Cl, 14.92. Found: C, 60.87; H, 5.08; N, 5.78; Cl, 14.69.

EXAMPLE 3

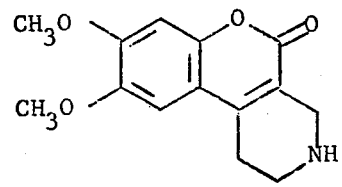

1,2,3,4-Tetrahydro-8,9-dimethoxy-5H-[1]benzopyrano[3,4c]pyridin-5-one Hydrochloride. The title compound was prepared by the procedure described in example 2. From 46.0 g (0.3m) of 3,4-dimethoxyphenol, 41.7 g (0.2m) of 3-carbethoxy-4-piperidone hydrochloride and 100 ml of 73% v/v sulfuric acid, there was obtained 33.4 g (63%) of the pyridin-5-one as the hydrochloride, mp 254°–6°C.

Anal. Calcd for $C_{14}H_{15}NO_4 \cdot HCl \cdot ½H_2O$: C, 54.82; H, 5.59; N, 4.57; Cl, 11.56. Found: C, 54.73; H, 5.91; N, 4.38; Cl, 11.64.

EXAMPLE 4

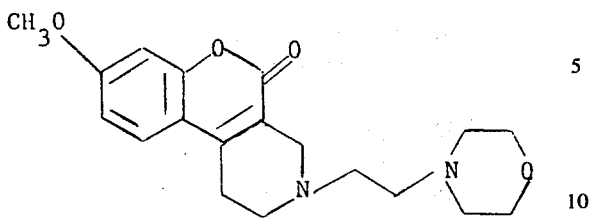

1,2,3,4-Tetrahydro-8-methoxy-3-(2-morpholinoethyl)-5H-[1]benzopyrano[3,4-c]pyridin-5-one. A mixture of 10 g (0.043 m) of 1,2,3,4-tetrahydro-8-methoxy-5H-[1]benzopyrano[3,4-c]pyridin-5-one, 11.2 g (0.06 m) of N-(2-chloroethyl)-morpholine HCl and 14.2 g of triethylamine (0.14 m) in 170 ml of abs. EtOH was refluxed with stirring and protection from mositure for 4 hours. The reaction was filtered hot, cooled slightly and treated with dry HCl. The resulting precipitate was filtered and washed with EtOH, then ether; yield 14.6 g (81%). Crystallization from methanol afforded analytical material, mp 237°–40°C.

Anal. Calcd for $C_{19}H_{24}N_2O_4 \cdot 2HCl$: C, 54.68; H, 6.28; N, 6.71; Cl, 16.99. Found: C, 54.42; H, 6.47; N, 6.65; Cl, 17.09.

EXAMPLE 5

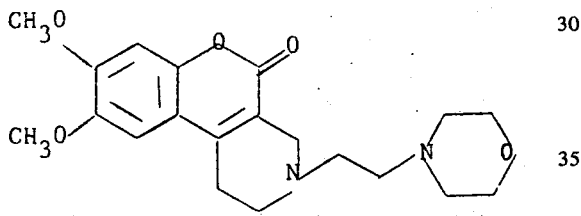

1,2,3,4-Tetrahydro-8,9-dimethoxy-3-(2morpholinoethyl)5H-[1]benzopyrano-[3,4-c]pyridin-5-one. A mixture of 7.85 g (0.03 m) of 1,2,3,4-tetrahydro-8,9-dimethoxy-5H-[1]benzopyrano[3,4-c]pyridin-5-one, 6.15 g (0.033 m) of N-(2-chloroethyl) morpholine HCl and 7.08 g (0.07 m) of triethylamine in 250 cc of ethanol was refluxed for 6 hr. and filtered hot. Treatment of the hot reaction solution with excess HCl 6 hr. and cooling to room temperature afforded crude product. Crystallization from 75% EtOH afforded analytical material mp. 238°–40°C.

Anal. Calcd for $C_{20}H_{26}N_2O_5 \cdot 2Hcl$: C, 53.70; H, 6.31; N, 6.26; Cl, 15.85. Found: C, 53.60; H, 6.47; N, 6.35; Cl, 15.66.

EXAMPLE 6

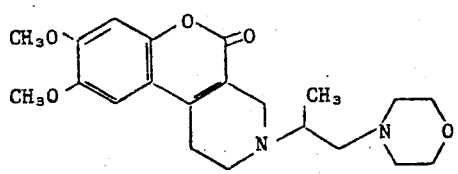

1,2,3,4-Tetrahydro-8,9-dimethoxy-3-(1-methyl-2-morpholinoethyl)-5H-[1]benzopyrano[3,4-c]pyridin-5-one. In the same way described in Example 5, .02 m of 1,2,3,4-tetrahydro-8,9-dimethoxy-5H-[1]benzopyrano[3,4-c]pyridin-5-one was alkylated with N-(2-chloropropyl)morpholine to give, after recrystallization from 95% EtOH 1.3 g of product; mp 228°–230°C.

Anal. Calcd for $C_{21}H_{28}N_2O_5 \cdot 2HBr$: C, 53.62; H, 6.43; N, 5.95; Br, 16.98. Found: C, 53.70; H, 6.39; N, 6.02; Br, 16.97.

EXAMPLE 7

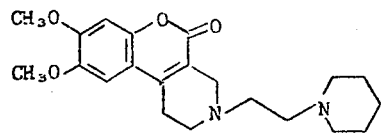

1,2,3,4-Tetrahydro-8,9-dimethoxy-3-(2-piperidinoethyl)-5H-[1]benzopyrano[3,4-c]pyridin-5-one. A solution of 14.4 g. (0.055 m) of 2° amine, 11.18 g. (0.0605 m) of N-(2-chloroethyl)piperidine hydrochloride and 12.2 g. (0.121 m) of triethylamine in 500 ml. of abs. EtOH was refluxed for 17½ hr. Hot filtration and immediate treatment with excess HCl gas afforded 19.5 g. of crude DiHCl salt. Dissolving in 1.4 l. of 95% EtOH, filtration, and boiling down to 400 cc afforded analytical material, m.p. 233°14 239°C.

Anal. Calcd for $C_{21}H_{28}N_2O_4 \cdot 2HCl$: C, 56.63; H, 6.79; N, 6.29; Cl, 15.92. Found: C, 56.37; H, 6.99; N, 6.24; Cl, 16.01.

EXAMPLE 8

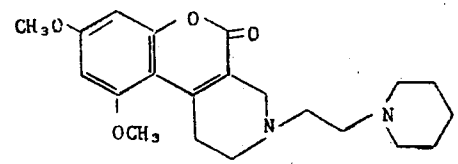

1,2,3,4-Tetrahydro-8,10-dimethoxy-3-(2-piperidinoethyl)-5H-[1]benzopyrano[3,4-c]pyridin-5-one. In the same way as described in Example 5, 0.02 m of 1,2,3,4-tetrahydro-8,10-dimethoxy-5H-[1]benzopyrano[3,4-c]pyridin-5-one was alkylated with N-(2-chloroethyl)-piperidine to give, after crystallization from MeOH, 3.0 g of product; mp 190°–224°C.

Anal. Calcd for $C_{21}H_{28}N_2O_4 2Hcl$: C, 56.63; H, 6.79; N, 6.29; Cl, 15.92. Found: 53.69; H, 6.30; N, 6.26; Cl, 14.74.

EXAMPLE 9

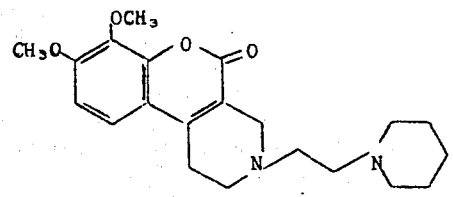

1,2,3,4-Tetrahydro-7,8-dimethoxy-3-(2-piperidinoethyl)-5H-[1]benzopyrano[3,4-c] pyridin-5-one. In the same way as described in Example 5, 5.7 mmoles of 1,2,3,4-tetrahydro-7,8-dimethoxy-5H-[1]benzopyrano[3,4-c]pyridin-5-one was alkylated with N-(2-chloroethyl)-piperidine to give, after recrystallization from MeOH, 0.5 g of product; mp 236°–239°C.

Anal. Calcd for $C_{21}H_{28}N_2O_4 \cdot 2HCl$: C, 56.63; H, 6.79; N, 6.29; Cl, 15.92. Found: C, 55.58; H, 6.77; N, 6.30; Cl, 15.68.

EXAMPLE 10

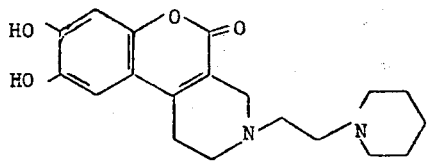

1,2,3,4-Tetrahydro-8,9-dihydroxy-3-(2-piperidinoethyl)-5H-[1]benzopyrano[3,4-c]pyridin-5-one. A solution of 4.7 g of 1,2,3,4-tetrahydro-8,9-dimethoxy-3-(2-piperidinoethyl)-5H-[1]benzopyrano[3,4-c]pyridin-5-one in 70 cc of 48% HBr was refluxed for 17 hr and cooled. Precipitate was cryst from water affording 2.8 g of product; mp 291°–295°C.

Anal. Calcd for $C_{19}H_{24}N_2O_4 \cdot 2HBr$: C, 45.08; H, 5.18; N, 5.53; Br, 31.57. Found: C, 45.06; H, 5.30; N, 5.38; Br, 31.39.

EXAMPLE 11

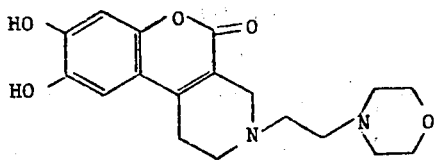

1,2,3,4-Tetrahydro-8,9-dihydroxy-3-(2-morpholinoethyl)-5H-[1]benzopyrano[3,4-c]pyridin-5-one. A solution of 8.7 g of 1,2,3,4-tetrahydro-8,9-dimethoxy-3-(2-morpholinoethyl)-5H[1]benzopyrano[3,4-c]pyridin-5-one in 60 cc of 48% HBr was refluxed for 17 hr then cooled. Crystallization of precipitate from water afforded 5.5 g of product; mp 299°–302°C.

Anal. Calcd for $C_{18}H_{22}N_2O_5 \cdot 2HBr$: C, 42.54; H, 4.76; N, 5.51; Br, 31.45. Found: C, 42.29; H, 4.72; N, 5.53; Br, 31.42.

EXAMPLE 12

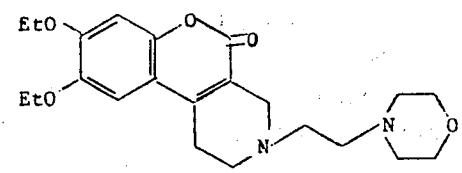

8,9-Diethoxy-1,2,3,4-tetrahydro-3-(2-morpholinoethyl)-5H-[1]benzopyrano[3,4-c]pyridin-5-one. A mixture of 0.01 m of 1,2,3,4-tetrahydro-8,9-dihydroxy-3-(2-morpholinoethyl)-5H-[1]benzopyrano[3,4-c]pyridin-5-one, 0.022 m of diethylsulfate, and 0.1 m of $K_2CO_3$ in 500 ml of acetone was refluxed for 18 hr, filtered hot and evaporated. Residue was dissolved in $CHCl_3$ and washed with 3% NaOH soln. $CHCl_3$ soluble material was crystallized from MeOH containing an excess of HCl gas affording 1 g of product; mp 240°–260°C.

Anal. Calcd for $C_{22}H_{30}N_2O_5 \cdot 2HCl$: C, 55.58; H, 6.78; N, 5.89; Cl, 14.91. Found: C, 55.38; H, 6.86; N, 5.98; Cl, 14.89.

EXAMPLE 13

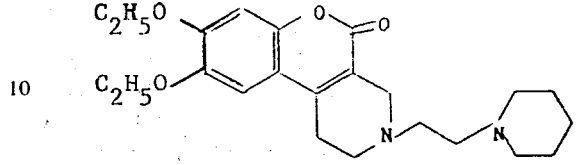

8,9-Diethoxy-1,2,3,4-tetrahydro-3-(2-piperidinoethyl)-5H-[1]benzopyrano[3,4-c]pyridin-5-one. A mixture of 0.01 m of 1,2,3,4-tetrahydro-8,9-dihydroxy-3-(2-piperidinoethyl)-5H-[1]benzopyrano[3,4-c]pyridin-5-one, 0.022 m of diethylsulfate and 0.1 m $K_2CO_3$ in 250 cc of acetone was refluxed for 20 hr and filtered hot. After evaporation, the residue was crystallized twice from EtOAc affording 0.6 g of product; mp 144°–146°C.

Anal. Calcd for $C_{23}H_{32}N_2O_4$: C, 68.97; H, 8.05; N, 7.00. Found: C. 68.62; H, 8.07; N, 7.03.

EXAMPLE 14

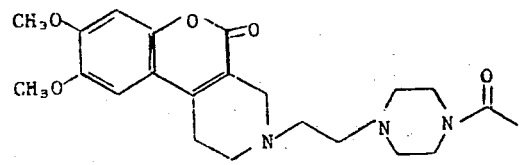

3-[2-(4-acetyl-1-piperazinyl)ethyl]-1,2,3,4-tetrahydro-8,9-dimethoxy-5H-[1]benzopyrano[3,4-c]pyridin-5-one. In the same way as described in Example 5, 0.02 m of 1,2,3,4-tetrahydro-8,9-dimethoxy-5H-[1]benzopyrano[3,4-c]pyridin-5-one was alkylated with N-acetyl-N'-(2-chloroethyl)piperazine to give, after recrystallization from MeOH, 5.8 g of product; mp 234°–235°C.

Anal. calcd for $C_{22}H_{29}N_3O_5 \cdot 2HCl$: C, 54.10; H, 6.40; N, 8.60; Cl, 14.52. Found: C, 54.09; H, 6.42; N, 8.75; Cl, 14.50.

We claim:
1. A method for producing bronchodilation in a mammal in need thereof which comprises the administration of an effective amount of a compound of the formula:

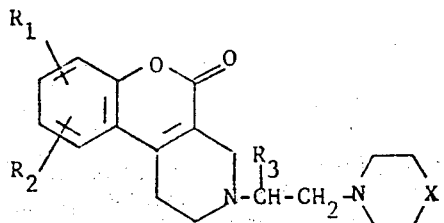

I wherein $R_1$ and $R_2$ are hydrogen, hydroxyl or lower alkoxyl of from 1 to 6 carbon atoms; $R_3$ is hydrogen or lower alkyl of 1 to 6 carbon atoms and x is oxygen, sulfur, methylene or nitrogen substituted by hydrogen, lower alkyl of 1 to 6 carbon atoms or lower alkanoyl of 1 to 6 carbon atoms, to said mammal.

2. The method of claim 1 wherein the compound is 1,2,3,4-tetrahydro-8-methoxy-3-(2-morpholinoethyl)-5H-[1]benzopyrano[3,4-c]pyridin-5-one.

3. The method of claim 1 wherein the compound is 1,2,3,4-tetrahydro-8,9-dimethoxy-3-(2-morpholinoethyl)-5H-[1]benzopyrano[3,4-c]pyridin-5-one.

4. The method of claim 1 wherein the compound is 1,2,3,4-tetrahydro-8,9-dimethoxy-3-(1-methyl-2-morpholinoethyl)-5H-[1]benzopyrano[3,4-c]pyridin-5-one.

5. The method of claim 1 wherein the compound is 8,9-diethoxy-1,2,3,4-tetrahydro-3-(2-morpholinoethyl)-5H-[1]benzopyrano[3,4-c]pyridin-5-one.

6. The method of claim 1 wherein the compound is 1,2,3,4-tetrahydro-8,9-dimethoxy-3-(2-piperidinoethyl)-5H-[1]benzopyrano[3,4-c]pyridin-5-one.

7. The method of claim 1 wherein the compound is 1,2,3,4-tetrahydro-8,10-dimethoxy-3-(2-piperidinoethyl)-5H-[1]benzopyrano[3,4-c]pyridin-5-one.

8. The method of claim 1 wherein the compound is 1,2,3,4-tetrahydro-7,8-dimethoxy-3-(2-piperidinoethyl)-5H-[1]benzopyrano-[3,4-c]pyridin-5-one.

9. The method of claim 1 wherein the compound is 8,9-diethoxy-1,2,3,4-tetrahydro-3-(2-piperidinoethyl)-5H-[1]benzopyrano[3,4-c]pyridin-5-one.

10. The method of claim 1 wherein the compound is 3-[2-(4-acetyl-1-piperizinyl)ethyl]-1,2,3,4-tetrahydro-8,9-dimethoxy-5H-[1]benzopyrano[3,4-c]pyridin-5-one.

* * * * *